US010314570B2

(12) United States Patent
Watschke et al.

(10) Patent No.: US 10,314,570 B2
(45) Date of Patent: Jun. 11, 2019

(54) SURGICAL NEEDLE SYSTEM WITH ANCHOR RETENTION FEATURES

(75) Inventors: Brian P. Watschke, Minneapolis, MN (US); James R. Mujwid, Crystal, MN (US); James A. Alexander, Excelsior, MN (US); Justin M. Crank, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1106 days.

(21) Appl. No.: 14/343,843

(22) PCT Filed: Sep. 10, 2012

(86) PCT No.: PCT/US2012/054492
§ 371 (c)(1),
(2), (4) Date: Mar. 7, 2014

(87) PCT Pub. No.: WO2013/036949
PCT Pub. Date: Mar. 14, 2013

(65) Prior Publication Data
US 2014/0228863 A1      Aug. 14, 2014

Related U.S. Application Data

(60) Provisional application No. 61/532,262, filed on Sep. 8, 2011.

(51) Int. Cl.
| | |
|---|---|
| *A61B 17/04* | (2006.01) |
| *A61F 2/00* | (2006.01) |
| *A61B 17/06* | (2006.01) |
| *A61B 17/00* | (2006.01) |

(52) U.S. Cl.
CPC .... *A61B 17/0401* (2013.01); *A61B 17/06109* (2013.01); *A61F 2/0045* (2013.01); *A61B 2017/00477* (2013.01); *A61B 2017/00805* (2013.01); *A61B 2017/00986* (2013.01); *A61B 2017/0403* (2013.01); *A61B 2017/0409* (2013.01); *A61B 2017/0411* (2013.01);
(Continued)

(58) Field of Classification Search
CPC .......... A61B 17/0401; A61B 17/06109; A61B 2017/0409; A61B 2017/00805; A61B 2017/0424; A61F 2/0045
See application file for complete search history.

(56) References Cited

U.S. PATENT DOCUMENTS 5,141,520 A * 8/1992 Goble ................ A61B 17/0401
606/104
5,203,864 A * 4/1993 Phillips ................ A61B 17/064
227/137
(Continued)

FOREIGN PATENT DOCUMENTS

WO    WO 2010093421 A2 *  8/2010   ....... A61B 17/06109

*Primary Examiner* — Anh T Dang
(74) *Attorney, Agent, or Firm* — Brake Hughes Bellermann LLP

(57) ABSTRACT

Various surgical tissue anchor retention mechanisms, systems and methods are provided. The mechanisms, systems and methods can include a delivery tool or needle having a flex joint, a snap-fit, a cam and follower, a rotating tip, an expandable lock, a coil, an inverted collet, a tab, a buckling tube, an inflation element or like anchor retention or securement features.

11 Claims, 9 Drawing Sheets

(52) U.S. Cl.
    CPC ............... *A61B 2017/0427* (2013.01); *A61B 2017/0461* (2013.01)

(56) References Cited

U.S. PATENT DOCUMENTS

| | | | |
|---|---|---|---|
| 6,409,739 B1* | 6/2002 | Nobles | A61B 17/11 |
| | | | 606/148 |
| 9,226,809 B2* | 1/2016 | VanDeWeghe | A61B 17/06109 |
| 2001/0049529 A1* | 12/2001 | Cachia | A61B 17/68 |
| | | | 606/301 |
| 2003/0120292 A1* | 6/2003 | Park | A61B 17/083 |
| | | | 606/153 |
| 2007/0293935 A1* | 12/2007 | Olsen | A61F 2/95 |
| | | | 623/1.12 |
| 2009/0287229 A1* | 11/2009 | Ogdahl | A61B 17/0401 |
| | | | 606/151 |

* cited by examiner

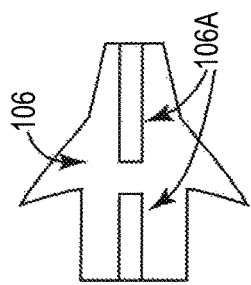
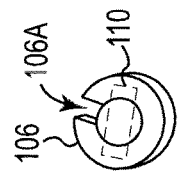
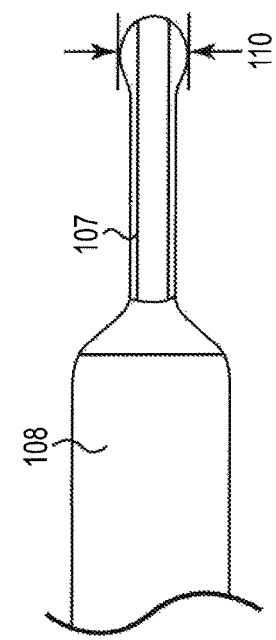
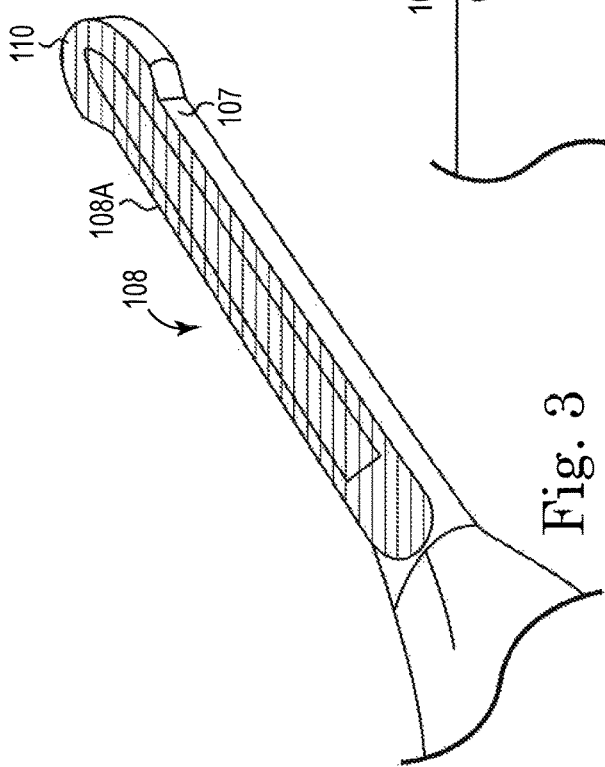
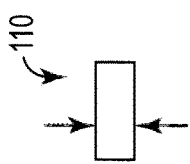

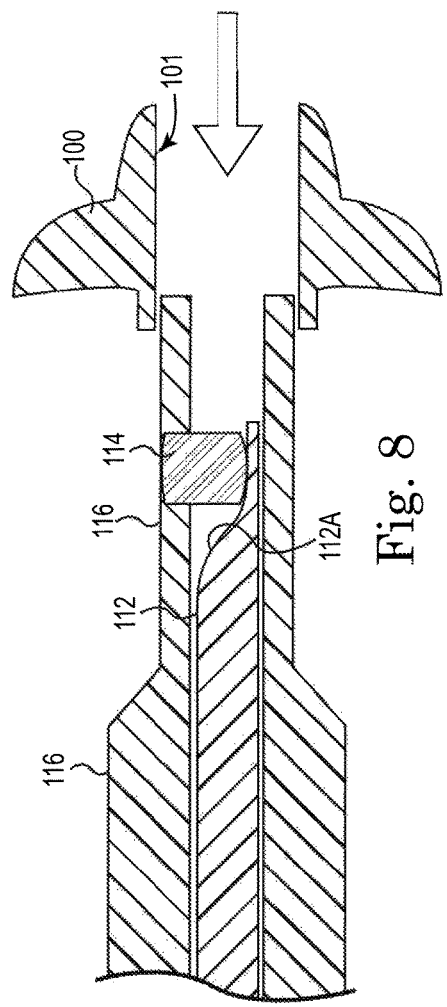
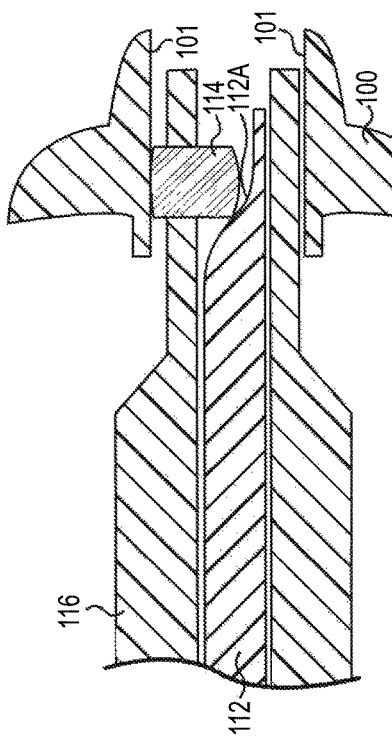

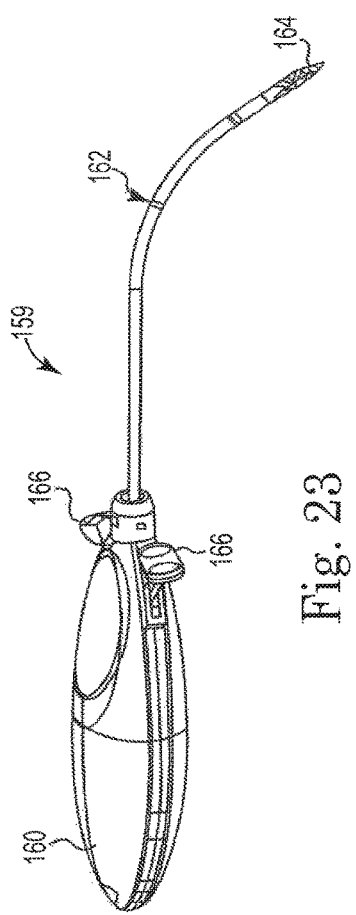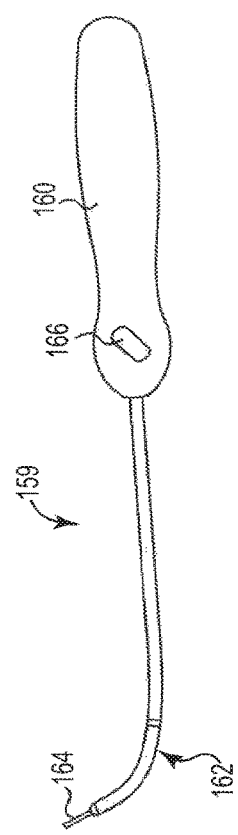

SURGICAL NEEDLE SYSTEM WITH ANCHOR RETENTION FEATURES

PRIORITY

This Application claims priority to and the benefit of U.S. Provisional Patent Application No. 61/532,262, filed Sep. 8, 2011, which is incorporated herein by reference in its entirety.

FIELD OF THE INVENTION

The present invention relates generally to surgical methods and apparatus and, more specifically, to surgical needle configurations, systems and methods adapted to selectively engage one or more implant anchors.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

A specific area of pelvic health is trauma of the pelvic floor, e.g., of the levator ("levator ani") or coccygeus muscle (collectively the pelvic floor). The pelvic floor is made up of the levator and coccygeus muscles, and the levator is made up of components that include the puborectalis muscle, the pubococcygeus muscle, and the iliococcygeous muscle. For various reasons, the levator may suffer weakness or injury such as damage to the levator hiatus, ballooning or levator avulsion, any of which that can result in symptoms such as prolapse, fecal incontinence, and other conditions of the pelvis.

Levator defects (weakness or injury) can affect any portion of the levator, and can be especially common in the pubic portion of the levator ani, including the pubococcygeus and puborectalis muscles. Such defects are relatively common, for instance, in women with vaginal prolapse. Defects can also be present at the iliococcygeus muscle. Still other defects are in the form of a paravaginal defect, such as avulsion of the inferiomedial aspects of the levator ani from the pelvic sidewall; avulsion can refer to tissue being detached from the pubic bone, and may precede prolapse conditions. Another levator defect is levator ballooning, which refers to distension of levator muscles.

A different levator defect is a defect of the levator hiatus, which can reduce the stability of the pelvic floor and may result in sexual dysfunction, defecatory dysfunction, rectal prolapse, and fecal incontinence. Levator hiatus is also believed to play a significant role in the progression of prolapse.

There is a desire to obtain a minimally invasive yet highly effective anchoring system for implants that can be used to treat incontinence, pelvic organ prolapse and other conditions. There is also a desire to provide improved mechanisms, systems and methods to retain tissue anchors to delivery tools for the use in placing implants in the patient.

SUMMARY OF THE INVENTION

Various improved surgical tissue anchor retention mechanisms, systems and methods are provided. The mechanisms, systems and methods can include a delivery or introduction needle tool having a flex joint, a snap-fit, a cam and follower, a rotating tip, an expandable lock, a coil, and inverted collet, a tab, a buckling tube, an inflation element or like anchor retention features.

In certain embodiments, a surgical introducer needle and anchor kit or system includes an implantable support apparatus, such as a sling, mesh or straps, a needle assembly having a handle assembly, and one or more anchoring devices generally provided at one or more ends of the support apparatus. Each anchor device can be adapted for attachment to tissue within the pelvis of a patient such that attachment to the patient tissue allows for selective placement of the support apparatus to support the patient's bladder, urethra or other organs or tissue. The handle and needle assemblies are adapted to operatively and selectively engage and direct the anchors and support apparatus of the system according to the various embodiments disclosed herein.

The needle and anchoring assemblies can be configured to provide increased precision, reliability and usefulness in engaging an anchor device or implant, and retracting the needle, or a portion thereof, from the anchor upon deployment. Various embodiments of the needle system of the present invention can include a handle operatively coupled with a cannulated needle and an internal wire or like structure or member such that a distal tip of the wire is selectively engageable with and retractable or otherwise disengageable from the implant or anchor. The internal wire and the respective distal tip can be retractable or otherwise controlled within the needle by way of at least one actuator, e.g., a button or slider actuator.

Still other embodiments of the handle assembly can include a clicker or toggle mechanism as the at least one actuator to selectively toggle in operative communication with a wire, member or the distal needle tip to facilitate selective engagement and disengagement with the anchor or implant.

Various anchor systems can be included to provide security so that the anchor will not easily detach or disengage from the needle during insertion, while still allowing for accurate placement and detachment of the anchor from the needle during deployment of the anchor e.g., within soft tissue within the pelvic region of a patient. For instance, retraction of the needle, or a portion thereof, from the anchor promotes stable and accurate positioning because the anchor is not forced or pushed off of the needle device until introduction and deployment is achieved.

Embodiments of the present invention may be incorporated into or provided with various commercial products marketed by American Medical Systems of Minnetonka, Minn., as the MiniArc® Single-Incision Sling and like implant or anchoring systems

BRIEF DESCRIPTION OF THE DRAWINGS

FIG. 3 is a partial schematic view of a snap-fit feature to secure an anchor to the tip of a delivery tool or needle, in accordance with embodiments of the present invention.

FIG. 4 is a partial schematic side view of a snap-fit feature to secure an anchor to the tip of a delivery tool or needle, in accordance with embodiments of the present invention.

FIG. 5 is a partial schematic view of an anchor with one or more slots, in accordance with embodiments of the present invention.

FIG. 6 is a partial schematic front view of a bulb feature for a delivery tool or needle, in accordance with embodiments of the present invention.

FIG. 7 is a partial schematic view of a bulb feature securing an anchor to the tip of a delivery tool or needle, in accordance with embodiments of the present invention.

FIGS. 8-9 are partial schematic cross-section views of a cam and follower feature to secure an anchor to the tip of a delivery tool or needle, in accordance with embodiments of the present invention.

FIGS. 23-24 are schematic views of exemplary implant delivery or needle devices, in accordance with embodiments of the present invention.

DETAILED DESCRIPTION OF PREFERRED EMBODIMENTS

The various embodiments of the present invention can include a needle delivery or introduction device and one or more anchor devices. In general, the needle introduction device is adapted to deliver and deploy a mesh implant or sling device. The implant or sling can include the one or more anchor devices adapted to engage with target tissue such that the implant can be positioned to provide support to treat pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle or ligament weakness. Other uses can include providing a support or platform for plastic surgery, hernia repair, and ortho repairs and support, to name a few. Embodiments of the implants can include a tissue support portion and one or more extending arms or anchoring portions.

Figure 1:
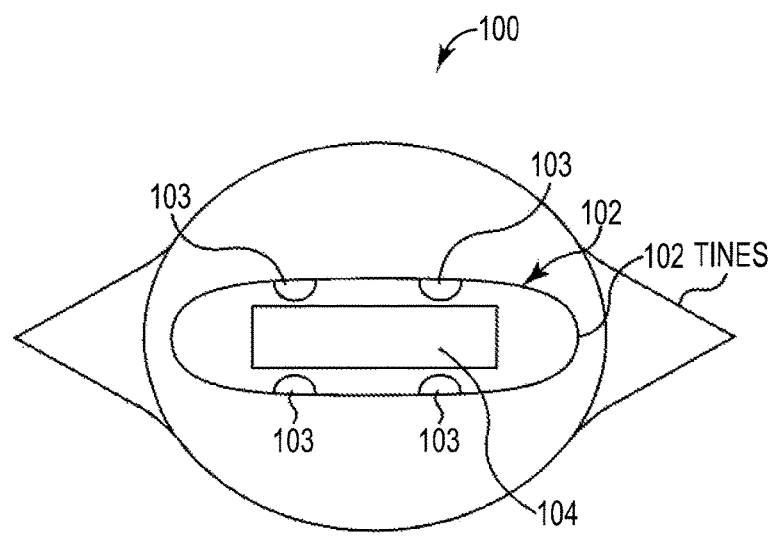
FIG. 1 is a schematic front view of a flex joint feature to secure an anchor to the tip of a delivery tool or needle, in accordance with embodiments of the present invention.
Figure 2:
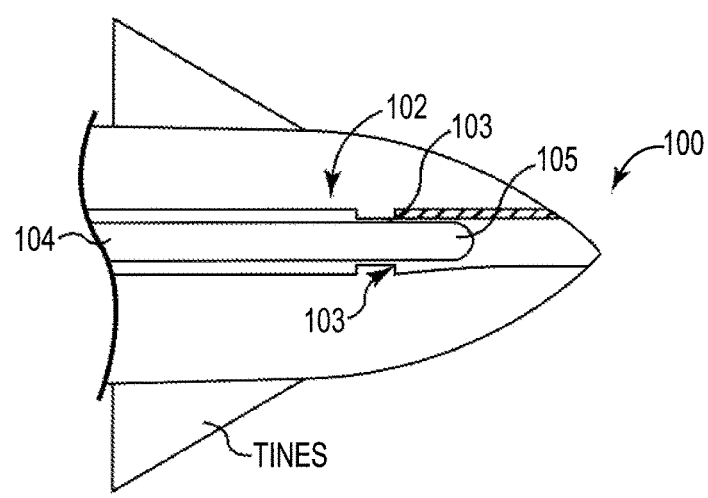
FIG. 2 is a partial schematic side view of a flex joint feature to secure an anchor to the tip of a delivery tool or needle, in accordance with embodiments of the present invention.

Referring generally to FIGS. 1-2, a flex joint anchor device 100 is shown. The anchor 100 provides a means to lock a sling or other implant to the tip 105 of a delivery tool 104 and to deploy the anchor 100. This configuration includes flexible joint features 102 that utilize material deformation to apply frictional force via friction pins 103 to secure or lock a portion of the anchor 100 to the delivery tool 104—e.g., sliding the anchor 100 onto the tip 105. In these figures the exemplary tip 105 of the delivery tool 104 is depicted. However, other delivery tools can be utilized without departing from the scope of the invention. This embodiment provides flexibility and does not depend on tight tolerances as the material construct of the features 102 can be adapted to provide a level of "give" or deformation. As such, passive anchor securement or locking is provided.

Referring generally to FIGS. 3-7, a snap-fit anchor device 106 is shown. The snap fit anchor 106 provides a means to secure or lock a sling or other implant to the tip 107 of a delivery tool 108 to facilitate deployment of the anchor 106. This configuration includes an anchor 106 that can include slot features 106a—e.g., on one or more ends 109 of the anchor 106. The delivery tool 108, such as a needle or like implant introduction device, is configured with a bulb portion 110, such as at the tip 107, with the anchor 106 adapted to slide onto or otherwise engage with the tip 107. A portion of the shaft of the delivery tool can be keyed, e.g., including a flat portion 108a, in cross-section to facilitate orientation and securement. The keyed portion 108a allows the needle tip 107 and/or bulb 110 to pass through the one or more slot features 106a such that the anchor 106 can engage and secure to the needle tip 107 via the bulb portion 110. In certain embodiments, such as that shown in FIG. 7, the needle can be rotated upon exiting the end of the anchor 106 such that the bulb 110 rotates to secure the anchor 106 in place. This configuration can eliminate the need for providing tight needle and anchor tolerances to maintain retention. It also provides for simplicity and reliability of use, and ease of manufacture.

FIGS. 8-9 show a cam and follower anchor retention mechanism for use with embodiments of the present invention. A cam 112 and a follower 114 mechanism or device can be contained inside of the needle tip 116 to secure or lock the anchor 100 to the needle tip 116. The shape, size and construct of the cam 112 can limit the amount or degree that the follower 114 protrudes from the side of the needle. In certain embodiments, the cam can include a taper or incline surface portion 112a adapted to provide a ramp or traveling surface for the follower device 114. For instance, depending on the internal diameter or clearance/engagement opening within the anchor 100 (e.g., aperture 101 adapted to receive the needle tip 116), embodiments of the cam 112 and follower 114 can take on different constructs to facilitate appropriate and desired engagement or locking of the anchor 100 to the needle tip 116. Engagement of the follower 114 with the anchor inside aperture diameter 101 provides the securement or locking. Upon sliding the anchor 100 onto the tip 116, the cam 112 pushes the follower 114 outward, pushing against the inside diameter 101 of the anchor 100. The corresponding friction caused by the follower 114 within the aperture 101 keeps the anchor secured or locked to the needle tip 116.

Figure 10:
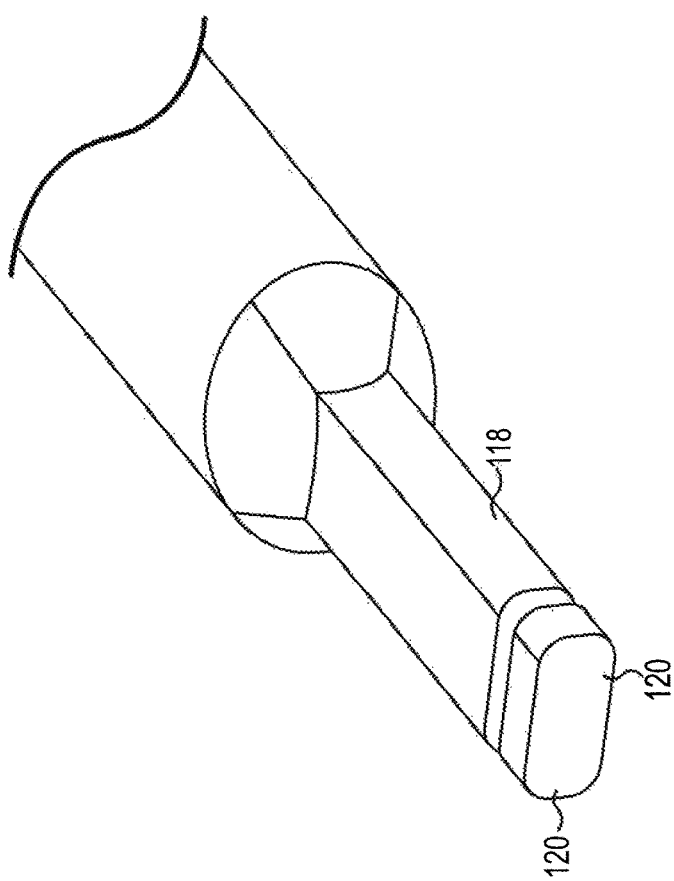
FIGS. 10-11 are partial schematic views of a rotating tip anchor retention feature of a delivery tool or needle, in accordance with embodiments of the present invention.
Figure 11:
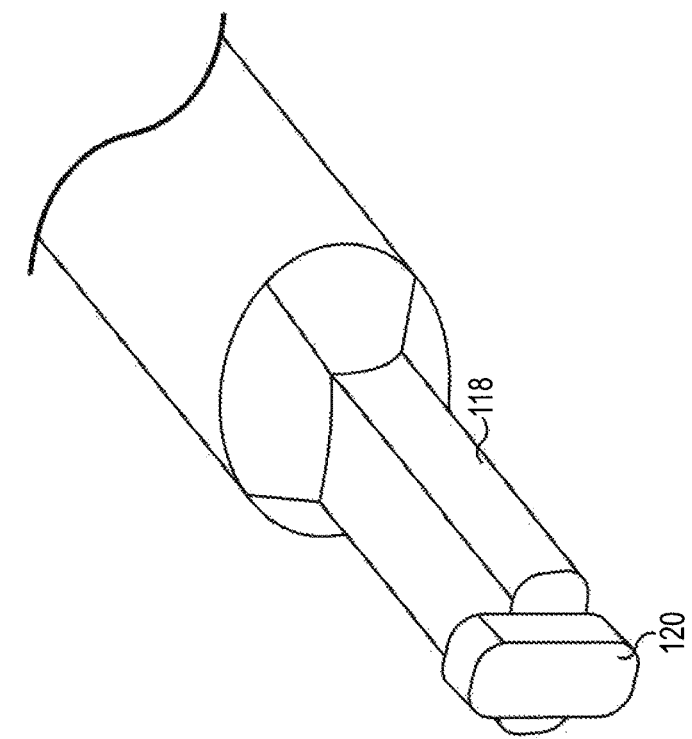

Referring generally to FIGS. 10-11, an introduction needle tool with a rotating tip and anchor retention mechanism is shown. A member of an implant introduction or delivery tool, such as a needle body or tip portion 118 is provided with a rotating tip 120 on an end thereof. The tip 120 can be fixed to a wire or post that is rotatable inside of the needle body 118 via actuation or triggering at a proximal portion of the delivery tool, such as the handle 160 (e.g., FIGS. 23-24). An actuator 166 can be provided in the handle 160 or extending from the handle to activate rotation of the tip 120. A wire, rod or like extending member can be operatively connected between the handle and the rotating tip 120 (e.g., through a lumen in the needle) to activate or facilitate the rotation. In the unlocked state, as shown in FIG. 10, the anchor 100 is loaded onto the needle by slipping the anchor 100 over the rotating tip 120 of the needle, e.g., with the tip 120 generally extending outside the anchor 100. As shown in FIG. 11, when the tip is then rotated approximately 90 degrees in certain embodiments, it acts as a stop, preventing the anchor 100 from coming off the tip 120 of the needle. As such, the internal diameter or receiving aperture of the anchor 100 can be sized and shaped to accommodate the tip 120. Once the anchor 100 is engaged with the target tissue, the tip 120 can be rotated to generally match the shape of the needle body (e.g., FIG. 10), thus allowing the physician to pull back and disengage the needle from the anchor 100. The size, shape and construct of the rotating tip 120 can vary greatly according to particular use applications for the anchor and implant procedure.

Figure 13:
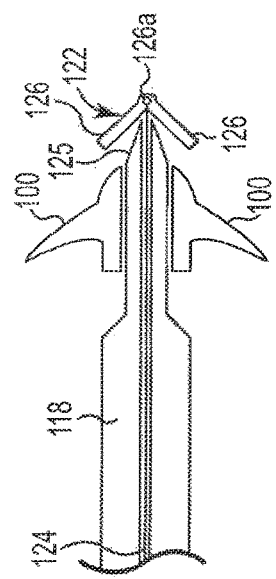
FIGS. 12-13 are partial schematic cross-section views of an expandable anchor retention feature of delivery tool or needle, in accordance with embodiments of the present invention.
Figure 12:
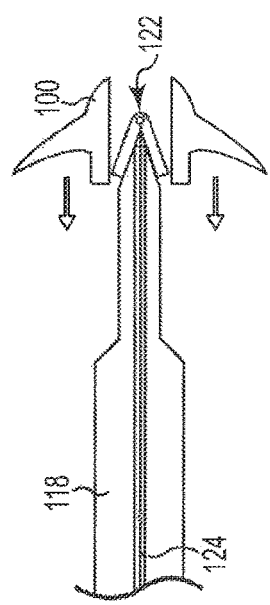

Referring generally to FIGS. 12-13, an expandable lock anchor retention mechanism is shown. An expandable lock device 122 is disposed at the end of a delivery tool, such as a needle tip 118. In an initial state, e.g., shown in FIG. 12, the device 122 is retracted, constrained or unlocked. The lock 122 is attached to a wire or member 124, which is attached to an actuator or like mechanism in or on the needle device (e.g., handle 160, actuator 166) that allows the user or physician to apply tension to the wire 124. Applying tension to the wire 124 pulls the lock against a stop or taper 125 at the end of the delivery tool, which causes the arms 126 of the lock to open about a pivot point or pin 126a. When the arms 126 of the lock 122 are in the open position, as shown in FIG. 13, they prevent the anchor 100 from slipping off the tip of the delivery tool. Once the anchor 100 is implanted or engaged with the target tissue site, the wire 124 can be pushed outward to collapse the arms 126 such that the lock device 122 can be pulled back through the anchor 100. The needle tip and body can then be retracted away from the target site.

Figure 14:
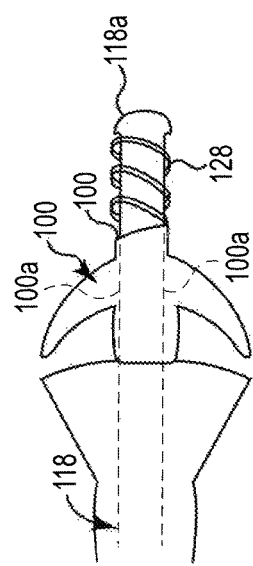
FIG. 14 is a partial schematic view of coil anchor retention feature of a delivery tool or needle, in accordance with embodiments of the present invention.

Referring generally to FIG. 14, a coil and an inverted collet lock anchor retention mechanism are shown. The coil feature 128 is disposed on or around the tip 118a of a delivery tool 118, such as the needle. The needle tip 118a can pass through the inner diameter or receiving aperture 100a of the anchor 100 and extend a distance beyond the tip of the anchor 100. The coil 128 can expand radially to lock the anchor 100 to the needle 118 (e.g., within the aperture of the anchor 100). The coil 128 can contract radially for the extended state to release the anchor 100 from the needle—e.g., becoming smaller than the inner diameter of the anchor aperture 100a. The anchor 100 can be disposed on the needle when the coil 128 is in the retracted or reduced state. An actuator mechanism (e.g., actuator 166) can be provided with the handle 160 of the introduction needle device to selectively actuate (e.g., pull in or push out) the contraction and expansion of the coil 128 via a wire or member. When the coil 128 is contracted, the anchor 100 can be inserted or removed from the tip 118a of the needle. When expanded, the coil 128 secures the anchor 100 to the needle or needle tip. For example, a plunger-type mechanism can provide longitudinal extension and retraction of the coil 128, thereby resulting in radial retraction and expansion, respectively. The coil 128 can be a component of the needle assembly or it can be integrated into the anchor 100. In an alternative, an elastomeric tube or member can be used instead of the coil 128. Like the coil 128, the tube expands and contracts radially in response to longitudinal compression and extension to facilitate engagement and disengagement with the anchor 100.

Figure 15:
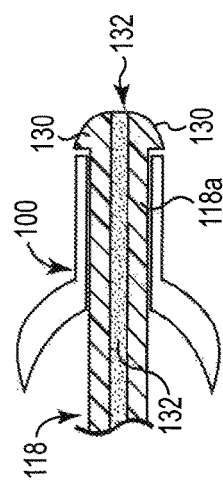
FIG. 15 is a partial schematic cross-section view of collet anchor retention feature of a delivery tool or needle, in accordance with embodiments of the present invention.

Referring to FIG. 15, collet jaws or members 130 can flex inward to allow the anchor 100 to be passed over. A straightening mandrel 132 may be disposed between the jaws 130 to facilitate the operation if the jaws 130 are biased inward. The mandrel 132 is pushed though the inside diameter of the collet to force the jaws 130 open. Thus, the mandrel 132 locks the jaws 130 in the expanded anchor-retaining position. The mandrel 132 can be selectively actuated from a remote location, such as in the handle or actuator (e.g., actuator 166) of a delivery tool. The mandrel 132 can be formed of a generally deformable or selectively-expandable material—such as polymer or metal.

Figure 19:
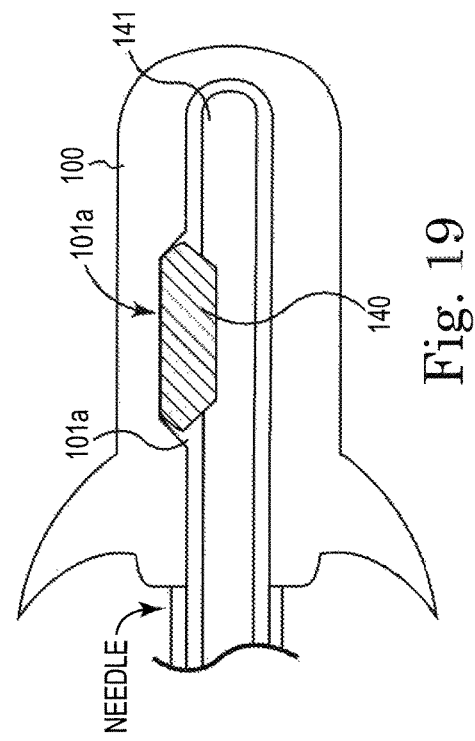
FIGS. 16-19 are partial schematic views of an expanding tab or buckling tube anchor retention feature of a delivery tool or needle, in accordance with embodiments of the present invention.

Referring generally to FIGS. 16-19, a protruding tab anchor retention mechanism is shown. A tab 134 can protrude or extend from a sidewall or like portion of the delivery tool or needle 133. A wire, rod or like cable member 136 can be attached to the end of the tab 134. When tension is applied to the wire 136, it pulls the tab 134 down or inward to allow the anchor 100 to be loaded onto the needle 133. When the tension in the wire 136 is released, the tab 134 biases outward and secures the anchor 100 to the needle 133. A cover, membrane or sheath 134a may also be provided over the tab 134 area to keep tissue material out, as shown in FIG. 19. The tab 134 and portions of the needle 133 can be constructed of shape memory polymer or metal material to provide the disclosed biasing and expansion properties. In other embodiments, the tab 124 can be spring biased.

Figure 18:
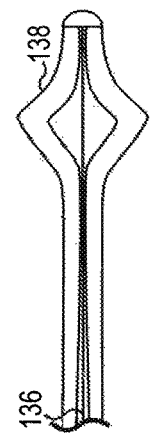

Referring to FIG. 18 in particular, a collapsing or buckling tube retention mechanism is shown. The wire 136 is attached to the end or other portion of a tube 138 and runs through the inside diameter of the tube 138 and attaches to an actuator mechanism or like device in the handle of the delivery tool. Tension applied to the wire 136 can cause the tube 138 to buckle and expand outwardly. Outward expansion of the tube 138 locks the anchor 100 to the delivery tool or needle tip. Releasing the tension in the wire 136, or pushing the wire 136 forward, generally straightens the tube 138 and allows the anchor 100 to release from the needle or tip, or to be initially received by the needle.

Figure 20:
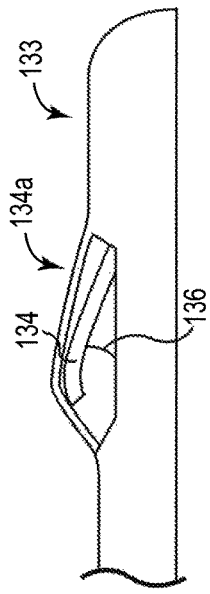
FIG. 20 is a partial schematic cross-section view of an inflatable element for securing an anchor to a delivery tool or needle, in accordance with embodiments of the present invention.
Figure 16:
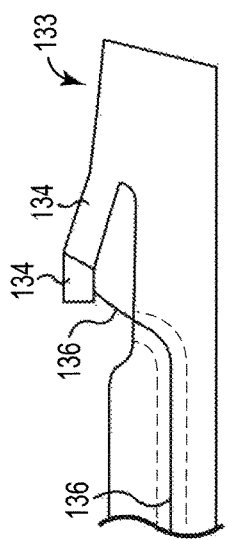
Figure 17:
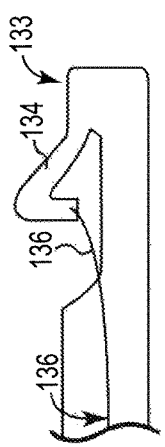

Referring to FIG. 20, a balloon, inflation or expansion lock retention mechanism or element is provided. The tip 141 of the delivery tool is provided with an inflatable element 140. The element 140 can be inflated (e.g., via fluid expansion actuator in the handle or needle portion) to protrude or expand into a recess or aperture 101a in the anchor 100, thereby securing or locking the anchor 100 to the tip 141. A membrane or sheath can be provided over the tool or needle region to keep blood and tissue out. The membrane can be constructed of a silicone or other suitable flexible material.

Figure 21:
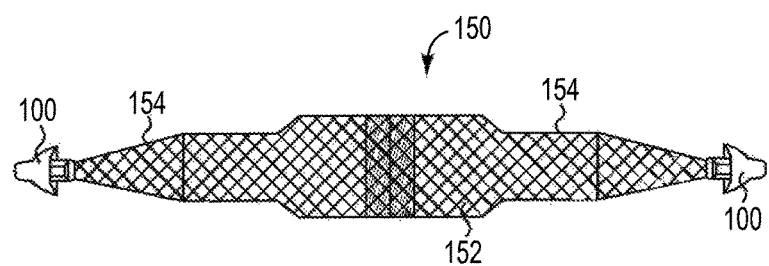
FIGS. 21-22 are schematic views of exemplary sling or implant devices, in accordance with embodiments of the present invention.
Figure 22:
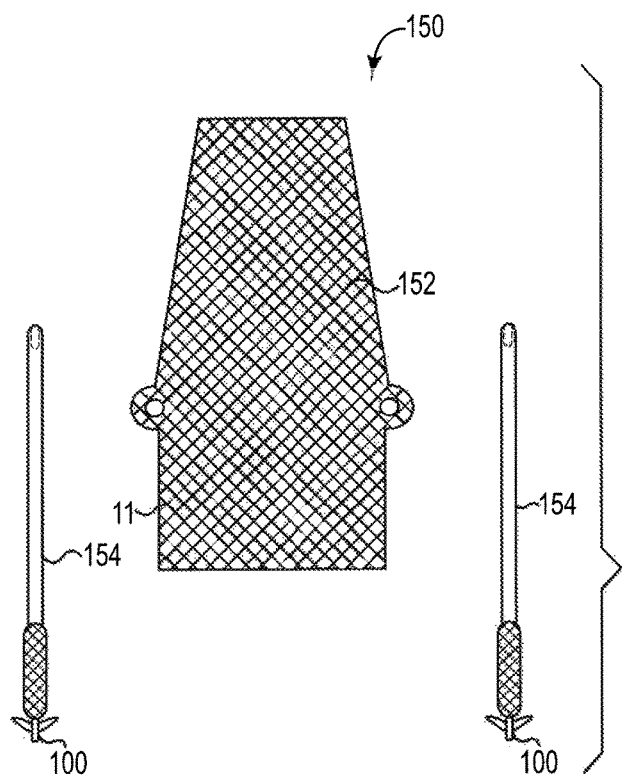

As shown in FIGS. 21-22, various embodiments of implantable sling or mesh devices 150 and methods adapted to include certain anchoring and other implant structures or devices are disclosed herein for use with the present invention. In general, the implant devices 150 can include a support portion 152, and extension or arm portions 154 having anchors 100 provided therewith. Various anchor 100 embodiments provided herein can include one or more extending tines or barbs to promote tissue engagement and fixation. The aperture or other engagement portion 101 can be included with the anchors 100 or devices 150 and adapted to selectively or releasably engage with or from the needle tips or end portions. Certain embodiments of the devices 150 can be constructed of or from a film or sheet material of polypropylene, polyethylene, fluoropolymers or like compatible materials.

As described herein, the various anchor and sling or implant devices can be deployed with various needle or introduction devices. Exemplary embodiments of introduction or needle devices 159 are provided in FIGS. 23-24. The needle devices can include a handle portion 160 and a needle length 162 that can be non-linear or curved in certain embodiments to facilitate deployment and navigation through tissue and around anatomical structure. In other embodiments, the needle devices can be generally straight, helical, or take on a myriad of other shapes and designs to facilitate deployment and use. A distal tip or portion 164 of the needle can receive or engage with the anchors of the present invention to facilitate deployment and tissue fixation. A wire, rod or like member can extend through a lumen of the needle and terminate at the distal tip portion 164, and operatively connect to the handle 160. The handle 160 can include one or more actuators 166 (e.g., slider, button, etc.) operatively connected to the needle length or tip, or wire, to selectively move (e.g., retract, extend, contract, or expand) the distal portion or tip of the needle. In such embodiments, the anchor (e.g., anchor 100) can be securely engageable with the distal tip of the needle such that activation of the one or more actuators 166 selectively disengages the anchor, or otherwise moves or actuates a securement or retention feature of the needle to selectively engage or disengage with the anchor.

The various implants or systems, mechanisms, devices, features and methods detailed herein are envisioned for use with many known implant and repair systems (e.g., for male and female), features and methods, including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261 and WO 2007/097994, and U.S. Patent Publication Nos. 2012/0157761, 2011/0144417, 2011/0124956, 2010/0105979, 2002/151762 and 2002/147382. Accordingly, the above-identified disclosures are fully incorporated herein by reference in their entirety.

The various components and portions of the devices and structures disclosed herein can be constructed of materials such as stainless steel, Nitinol and suitable plastics. Certain components or portions can be generally flexible, rigid, or a combination thereof.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

The invention claimed is:

1. An implant introduction system, comprising:
   a needle device including a handle, an actuator, a wire extending through a needle length, and a distal tip portion, the distal tip portion including a tapered portion, the tapered portion having a first surface and a second surface, the distal tip portion including an expansion feature which is attached to the wire and in operative communication with the actuator, the expansion feature including a first arm and a second arm, the first arm being movably coupled to the second arm, the expansion feature having a closed configuration in which an inner surface of the first arm contacts the first surface of the tapered portion and an inner surface of the second arm contacts the second surface of the tapered portion; and
   an implant including an anchor device having a body defining an aperture extending therethrough, the anchor device having at least one barb extending from the body of the anchor device, the anchor device configured to be coupled to the distal tip portion of the needle device,
   wherein the expansion feature in the closed position is configured to traverse through the aperture of the anchor device, the expansion feature being configured to transition to an open configuration to secure the anchor device to the distal tip portion.

2. The system of claim 1, wherein actuation of the actuator causes the first arm and the second arm to move between the closed configuration and the open configuration.

3. The system of claim 1, wherein the implant includes a mesh material.

4. The system of claim 1, wherein, in the open configuration, the inner surface of the first arm is disposed a distance away from the first surface of the tapered portion and the second arm is disposed a distance away from the second surface of the tapered portion.

5. The system of claim 1, wherein the first arm is linear along a length of the first arm.

6. An implant introduction system, comprising:
   a needle device including a handle, an actuator, a wire extending through a needle length, and a distal tip portion, the distal tip portion including a lock which is attached to the wire and in operative communication with the actuator, the lock having a first arm and a second arm, the first arm and the second arm being pivotally coupled to each other via a pin; and
   an implant including an anchor device having a body defining an aperture extending therethrough, the anchor device having at least one barb extending from the body, the anchor device configured to be coupled to the distal tip portion of the needle device,
   the lock configured to traverse through the aperture of the anchor device, the first arm and the second arm of the lock being selectively movable to secure the anchor device to the distal tip portion.

7. The system of claim 6, wherein the lock is configured to move between a closed configuration in which the first arm and the second arm are disposed proximate to each other and an open configuration in which the first and the second arm are disposed away from each other.

8. The system of claim 7, wherein, in response to the lock being in the open configuration, the first and second arms prevent the anchor device from being de-coupled from the distal tip portion of the needle device.

9. The system of claim 7, wherein the actuator is configured to move the lock between the closed configuration and the open configuration.

10. The system of claim 6, wherein the implant includes a mesh material.

11. The system of claim 6, wherein the distal tip portion includes a tapered portion, the tapered portion having a first surface and a second surface opposite to the first surface, the closed configuration being a position in which an inner surface of the first arm contacts the first surface of the tapered portion and an inner surface of the second arm contacts the second surface of the tapered portion.

* * * * *